United States Patent [19]

Barber

[11] Patent Number: 4,523,980

[45] Date of Patent: Jun. 18, 1985

[54] PROCESS FOR THE RECOVERY OF HIGH PURITY SQUARIC ACID

[75] Inventor: James J. Barber, West Newton, Mass.

[73] Assignee: The Halcon SD Group, Inc., New York, N.Y.

[21] Appl. No.: 645,975

[22] Filed: Aug. 31, 1984

[51] Int. Cl.$^3$ .............................................. C25C 1/00
[52] U.S. Cl. .................................. 204/59 R; 568/366; 568/381
[58] Field of Search .............. 204/59 R; 568/366, 381

[56] References Cited

U.S. PATENT DOCUMENTS 3,833,489  9/1974  Ercoli ..................................... 204/72
4,159,387  6/1979  Bellus .................................... 568/381

Primary Examiner—John F. Niebling
Attorney, Agent, or Firm—William C. Long; Riggs T. Stewart; Daniel R. Zirker

[57] ABSTRACT

A process is disclosed for the recovery of high purity squaric acid from squarate containing solids from the electrochemical cyclization of carbon monoxide, involving contacting the squaric acid containing product with a two-phase mixture of strong, nonoxidizing aqueous acid and an immiscible organic solvent, followed by separating the solid, substantially pure squaric acid from the resulting three-phase mixture.

9 Claims, No Drawings

PROCESS FOR THE RECOVERY OF HIGH PURITY SQUARIC ACID

BACKGROUND OF THE INVENTION

This invention relates to a process for the electrochemical production and efficient recovery of squaric acid. More particularly, the invention relates to a simple and economic process for the isolation and purification of squaric acid-containing solids, i.e. squarate salts and complexes, formed from the electrochemical cyclization of carbon monoxide.

DESCRIPTION OF THE PRIOR ART

The electrochemical preparation of squaric acid from a CO feedstock has been disclosed in U.S. Pat. No. 3,833,489 as well as in my U.S. Pat. No. 4,461,681. In the process disclosed in U.S. Pat. No. 3,833,489, squaric acid is recovered from the nonaqueous solvents in which it is formed only through a costly and involved sequence of steps. First, all the solvent is evaporated, leaving a residue comprising squarate salts and complexes, electrolyte, and the nonvolatile byproducts. Then, the resultant residue is treated with concentrated HCl to afford raw squaric acid. Finally, the raw squaric acid is purified by forming and isolating a copper squarate complex, then treating this complex with $H_2S$ to precipitate CuS, and isolating the pure squaric acid remaining in solution. This process, however, is both expensive, complex, and does not readily allow recycle of solvent and electrolyte to the electrolysis reactor, which is desirable for effective commercial operation.

U.S. Pat. No. 4,461,681, discloses that, in the presence of certain aliphatic nitrile solvents, a substantially insoluble squarate salt or complex is formed in high yields during electrolysis, and that the insoluble squarate salt or complex is also more easily separated from the electrolysis mixture, allowing simple and inexpensive recycling of solvent and electrolyte to the electrolysis cell. The resulting filtered solids contain about 25 to 30 weight percent squarate.

SUMMARY OF THE INVENTION

This invention involves an economic and efficient process for the effective isolation of squaric acid from squarate containing solids from the electrolytic cyclization of carbon monoxide, preferably while utilizing the nitrile solvents disclosed in U.S. Pat. No. 4,461,681. The process eliminates the need for the costly and complex steps described in the prior art, such as forming a copper squarate complex and treating the complex with $H_2S$. The process instead comprises contacting the squarate salt and complex containing product solids with a two phase mixture comprising (1) a nonoxidizing aqueous acid, e.g., a strong mineral acid such a HCl or $H_2SO_4$, (2) an immiscible organic solvent, preferably, a polar organic solvent, e.g., ethyl acetate or isobutyronitrile. The resulting reaction mixture separates into three distinct phases: an aqueous phase, a liquid organic phase, and a solid phase of substantially squaric acid product, which is separated, preferably by filtration or another conventional method, from the reaction mixture.

DETAILED DESCRIPTION OF THE INVENTION

As disclosed in U.S. Pat. No. 4,461,681, squaric acid can be formed from the electrochemical reduction of CO, preferably in the presence of a member of a class of nitrile solvents. The solids produced during electrolysis when done in the presence of nitrile solvents are composed of about 25 to 30 wt. % squarate as a salt or complex, as well as metal ions from the sacrificial anode (preferably magnesium or aluminum), and other organic and inorganic materials derived from the solvent, electrolyte, and CO. Treatment of these squarate containing solids with organic solvents such as acetone, methylene chloride, toluene, isobutyronitrile, or ethyl acetate unfortunately separates only small amounts of impurities from the squarate-containing solids. However, contacting the squarate containing solids with strong, non-oxidizing aqueous mineral acids, such as HCl and $H_2SO_4$, yields mixtures of squaric acid and viscous oils that are extremely difficult to handle and separate.

Surprisingly, I have found that squaric acid can be simply and inexpensively isolated from the solids formed by electrolysis of CO, particularly in aliphatic nitrile solvents such as those described in U.S. Pat. No. 4,461,681. The process comprises contacting the squarate-containing electrolysis solids at the same time with a solution of a strong aqueous nonoxidizing mineral acid (e.g. hydrochloric, sulfuric, and the like) and also with a solution comprising an immiscible organic solvent, preferably an immiscible polar organic solvent, e.g., branched or straight chained aliphatic acetates, nitriles and the like, most preferably ethyl acetate or isobutyronitrile. Such treatment causes both the inorganic salts and organic impurities to dissolve in either the aqueous or the organic phase, with only the substantially pure squaric acid remaining undissolved. The separation may be carried out at any temperature between the freezing point of the aqueous or organic phase (whichever is higher) and the boiling point of the aqueous or organic phase (whichever is lower). The process may also be carried out under pressure, although this would not normally confer any advantage. The resultant pure squaric acid can be separated by filtration or any other suitable means familiar to those skilled in the art. The squaric acid recovered is typically from about 85 to 99% pure, and may be further purified if so desired, by crystallization from aqueous acid.

The following examples are provided to illustrate this invention, and are not to be construed as limiting this invention in any way except as indicated by the appended claims.

EXAMPLE 1

Solids obtained from the electrolysis of CO in isobutyronitrile with tetrabutyl ammonium iodide electrolyte and a Mg anode following the procedure detailed in Example 1 of U.S. Pat. No. 4,461,681 contained 28.9 wt.% squarate and 15.1 wt.% Mg. These solids (3.050 g) were mixed with 20 ml 6N HCl and 20 ml isobutyronitrile, stirred at room temperature for 2 hours, and filtered. Recovered solids (0.807 g) analyzed as 89.9 wt.% squaric acid.

EXAMPLES 2–6

The procedure used in these examples was similar to that of Example 1. In each case the solid squarate salt was prepared by the procedure of Example 1 of U.S. Pat. No. 4,461,681. Details and results are given in the following table.

TABLE 1

| Example No. | Solids (g) | Solids (Wt. % squarate) | Acid (N, ml) | Solvent (ml) | Temp. (°C.) | Time (Hrs) | Recovery (g) | Recovery (Wt. % Squaric Acid) |
|---|---|---|---|---|---|---|---|---|
| 2 | 3.14 | 28.9 | HCl (6, 20.0) | IBN (20.0) | 50 | 2 | 0.79 | 96.5 |
| 3 | 3.15 | 28.9 | HCl (3, 20.0) | IBN (20.0) | 20–25 | 2 | 0.62 | 97.4 |
| 4 | 15.52 | 23.9 | HCl (6, 50.0) | IBN (50.0) | 20–25 | 4 | 3.40 | 97.1 |
| 5 | 50.0 | 33.2 | $H_2SO_4$ (8, 125.0) | IBN (125.0) | 20–25 | 2 | 16.20 | 99.8 |
| 6 | 10.0 | 32.5 | $H_2SO_4$ (8, 25.0) | EA (25.0) | 20–25 | 2 | 3.20 | 100.0 |

IBN = isobutyronitrile
EA = ethyl acetate

I claim:

1. A process for the isolation of substantially pure squaric acid from a squarate salt and complex containing product of the electrolytic cyclization of carbon monoxide, comprising:
   contacting the squarate salt and complex containing electrolysis product solid substantially at the same time with
   (1) a nonoxidizing aqueous acid, and
   (2) an immiscible organic solvent;
   separating the formed solid, substantially pure squaric acid from the resulting reaction mixture.

2. A process as claimed in claim 1 wherein the acid is a strong mineral acid.

3. A process as claimed in claim 2 wherein the acid is $H_2SO_4$ or HCl.

4. A process as claimed in claim 1 wherein the immiscible organic solvent is a polar organic solvent.

5. A process as claimed in claim 4 wherein the solvent is isobutyronitrile or ethyl acetate.

6. A process as claimed in claim 1 wherein the resulting reaction mixture comprises an aqueous phase, an organic phase, and a solid phase.

7. A process as claimed in claim 1 wherein the formed squaric acid is separated from the reaction mixture by filtration.

8. A process as claimed in claim 1 wherein the squaric acid product ranges from about 85 to 99% purity.

9. A process as claimed in claim 8 wherein the squaric acid product ranges from about 95–99% purity.

* * * * *